(12) United States Patent
Weikard et al.

(10) Patent No.: US 7,659,425 B2
(45) Date of Patent: Feb. 9, 2010

(54) PROCESS FOR PREPARING HYDROXYALKYL(METH) ACRYLATES USING LEWIS ACID CATALYSTS

(75) Inventors: Jan Weikard, Odenthal (DE); Christoph Gürtler, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 616 days.

(21) Appl. No.: 11/356,334

(22) Filed: Feb. 16, 2006

(65) Prior Publication Data

US 2006/0189823 A1 Aug. 24, 2006

(30) Foreign Application Priority Data

Feb. 22, 2005 (DE) ......................... 10 2005 008 032

(51) Int. Cl.
*C07C 67/26* (2006.01)
*C07C 69/52* (2006.01)

(52) U.S. Cl. ........................... 560/205; 560/93; 560/200

(58) Field of Classification Search .................. 560/93, 560/200, 205
See application file for complete search history.

(56) References Cited

U.S. PATENT DOCUMENTS

| | | | | |
|---|---|---|---|---|
| 4,069,242 A | 1/1978 | Gurgiolo | ...................... | 560/93 |
| 4,126,527 A | 11/1978 | Kaufman | ................ | 204/159.22 |
| 6,153,788 A | 11/2000 | Fischer et al. | ................ | 560/224 |
| 6,617,413 B1 | 9/2003 | Bruchmann et al. | ........... | 528/75 |

FOREIGN PATENT DOCUMENTS

GB 1 480 945 7/1977

OTHER PUBLICATIONS

Database CA [Online] Chemical Abstracts Service, Columbus, Ohio, US; Kimura, Kaoru et al: "Acrylate and methacrylate esters" XP002381405 gefunden im STN Database accession No. 1977:73371 * Zusammenfassung * & JP 51 086413 A (Toa Gosei Chemical Industry Co., Ltd., Japan) Jul. 29, 1976.
Analytical Sciences, vol. 17, Nov. 2001, pp. 1295-1299, Morikatsu Matsunaga et al, "Optimization of Conditions for Detailed Compositional Analysis of Acrylic Oligomers by Supercritical Fluid Chromatography with Temperature Programming or Modifier Gradient Technique".
Polymer, vol. 37, No. 20, (month unavailable) 1996, pp. 4629-4631, Michael A. Beckett et al, "Polymer Communications—A convenient n.m.r. method for the measurement of Lewis acidity at boron centres: correlation of reaction rates of Lewis acid initiated epoxide polymerizations with Lewis acidity".

*Primary Examiner*—Jafar Parsa
(74) *Attorney, Agent, or Firm*—Robert S. Klemz; Noland J. Cheung

(57) ABSTRACT

The present invention relates to a process for preparing hydroxyalkyl (meth)acrylates by reacting at least one compound A which contains at least one epoxide group with at least one compound B which contains at least one carboxylic acid group, wherein A and/or B also contains at least one (meth)acrylate group, in the presence of Lewis acid catalysts, each of which contains at least one directly bonded di(cyclo)alkylamino group.

19 Claims, No Drawings

PROCESS FOR PREPARING HYDROXYALKYL(METH) ACRYLATES USING LEWIS ACID CATALYSTS

BACKGROUND OF THE INVENTION

1. Field of the Invention

The present invention relates to a process for preparing hydroxyalkyl (meth)acrylates by reacting epoxides and carboxylic acids in the presence of Lewis acid catalysts.

2. Description of Related Art

In the context of the present invention, (meth)acrylate signifies the esters of acrylic acid, methacrylic acid or mixtures thereof. Hydroxyalkyl (meth)acrylates are used, inter alia, for reaction with isocyanate-containing compounds in order to prepare urethane (meth)acrylates, unsaturated polyurethane dispersions and dual cure hardeners for two-component or multi-component coating systems. The previously mentioned classes of compounds are used in particular as constituents of coating agents which cure by radical polymerization. This process can be triggered by actinic radiation. Curing via a combination of two reaction mechanisms is called dual cure by a person skilled in the art.

In order to obtain particularly highly cross-linked coatings, it is expedient to use compounds with high functionality, in particular with a large number of radically polymerizable double bonds, which can advantageously be produced by the use of hydroxyalkyl (meth)acrylates with a high functionality of acrylate and/or methacrylate groups. In order to facilitate the production of a targeted molecular structure, and thus, inter alia, a low viscosity, it is also expedient to use hydroxyalkyl (meth)acrylates in which the hydroxy functionality is distributed as narrowly as possible. Therefore, the preparation of hydroxyalkyl (meth)acrylates by the esterification of polyols such as trimethylolpropane or pentaerythritol with (meth)acrylic acid by a process which proceeds randomly and produces a wide distribution of hydroxy functionality, is disadvantageous.

Also, secondary products with high molecular weights are often formed. They have been identified as addition products of hydroxyl groups to the C—C double bonds of acrylates e.g. in Analytical Sciences, November 2001, vol. 17, p. 1295-1299. DE-A 19 860 041 discloses 3-acryloyloxy-2-hydroxypropyl methacrylate as a possible compound for reaction with polyisocyanates in order to produce dual cure hardeners. Details relating to the preparation of 3-acryloyloxy-2-hydroxypropyl methacrylate, however, are not described.

The preparation of 3-acryloyloxy-2-hydroxypropyl methacrylate by the reaction of glycidyl methacrylate with acrylic acid, both commercially available in high purity, and using a suitable catalyst, is described in the literature. Data on the purification/purity of the product are not given. Thus, EP-A 0 900 778 describes the reaction of excess acrylic acid in esterification reactions with glycidyl methacrylate, catalyzed by benzyltriethylammonium chloride.

3-acryloyloxy-2-hydroxypropyl methacrylate is also obtainable commercially in the fine chemical trade (Sigma-Aldrich Chemie GmbH, Taufkirchen, Germany), but the purity, determined by gel permeation analysis, is less than 60 wt. %; in particular, undesired high molecular weight fractions are found. The method of preparation is not disclosed.

A wide range of different catalysts for the reaction of glycidyl compounds with carboxylic acids is known from coating technology. This reaction is often used, for example, as a cross-linking reaction for curing lacquers. In addition to ammonium and phosphonium salts or amines and phosphines, certain metal compounds have also been described.

Certain properties of boron-containing Lewis acids are investigated in Polymer 1996, 37(20), 4629-4631. Their use as catalysts for epoxide-acid cross-linking reactions is mentioned. However, for reactions in the presence of (meth)acrylates, only catalysts which are catalytically active at low temperatures are suitable because otherwise there is a risk of the unwanted polymerization of the (meth)acrylates. Furthermore, greater selectivity of the catalysts is required for chemical synthesis as compared with a cross-linking reaction. Secondary reactions such as the Michael-analogous additions of hydroxyl or carboxyl groups to (meth)acrylates or hydroxyl-epoxide reactions lead to undesired secondary products because they have high molecular weights.

3-methacryloyloxy-2-hydroxypropyl methacrylate is sold with a purity greater than 85%, following purification by distillation, by Röhm GmbH, Darmstadt, Germany. The stability of the product is low and it has to be stored cold, which makes use on a commercially viable industrial scale difficult.

It is an object of the present invention to provide a process with which, for example, 3-acryloyloxy-2-hydroxypropyl methacrylate can be prepared, simply and at low temperatures, in high purity and without a costly purification process, i.e, without a concentration of high molecular weight or highly hydroxylated fractions.

It was found that the reaction of, for example, glycidyl methacrylate and acrylic acid, in bulk, proceeds rapidly and completely at temperatures of 80° C. by using catalysis with certain weak Lewis acid borane compounds, such as trisdimethylaminoborane.

SUMMARY OF THE INVENTION

The present invention relates to a process for preparing hydroxyalkyl (meth)acrylates by reacting at least one compound A which contains at least one epoxide group with at least one compound B which contains at least one carboxylic acid group, wherein A and/or B also contains at least one (meth)acrylate group, in the presence of Lewis acid catalysts, each of which contains at least one directly bonded di(cyclo)alkylamino group.

DETAILED DESCRIPTION OF THE INVENTION

Suitable compounds for use as compounds A are either monoepoxide compounds or polyfunctional epoxides, in particular di- or trifunctional epoxides. Examples include epoxidized olefins, glycidyl ethers of (cyclo)aliphatic or aromatic polyols and/or glycidyl esters of saturated or unsaturated carboxylic acids. Preferred monoepoxide compounds include glycidyl acrylate, glycidyl methacrylate, the glycidyl ester of versatic acid, butyl-glycidyl ether, 2-ethylhexyl-glycidyl ether, phenyl-glycidyl ether, o-cresyl-glycidyl ether or 1,2-epoxybutane. Glycidyl methacrylate is preferred.

Preferred polyepoxide compounds include polyglycidyl compounds of the bisphenol A or bisphenol F type as well as the perhydrogenated derivatives thereof or glycidyl ethers of polyfunctional alcohols such as butanediol, hexanediol, cyclohexanedimethanol, glycerol, trimethylolpropane or pentaerythritol.

It is also possible to use epoxy-functional polymers of vinyl monomers such as monofunctional acrylates, methacrylates or styrene along with the use of a proportion of e.g. glycidyl methacrylate.

Compounds B are either mono- or di- or higher functional carboxylic acids. Suitable monocarboxylic acids include saturated and preferably unsaturated carboxylic acids such as benzoic acid, cyclohexanecarboxylic acid, 2-ethylhexanoic acid, caproic acid, caprylic acid, capric acid, lauric acid, natural and synthetic fatty acids, and preferably acrylic acid, methacrylic acid, dimeric acrylic acid or crotonic acid. Suitable dicarboxylic acids include phthalic acid, isophthalic acid, tetrahydrophthalic acid, hexahydrophthalic acid, cyclohexane dicarboxylic acid, maleic acid, fumaric acid, malonic acid, succinic acid, glutaric acid, adipic acid, azelaic acid, pimelic acid, suberic acid, sebacic acid, dodecanedioic acid and hydrogenated dimeric fatty acids.

It is possible to use dicarboxylic acids in the form of their anhydrides, if available, with the addition of a corresponding amount of water. In addition to pure acids, acid-functional polyesters or corresponding reaction mixtures which have been prepared with an excess of acid may also be used. Such mixtures, in particular those containing polyether- and/or polyesteracrylates with e.g. excess acrylic acid are described, for example, in EP-A 0 976 716, EP-A 0 054 105 and EP-A 0 126 341.

It is also possible to use acid-functional polymers, e.g. polyacrylates, of vinyl monomers such as monofunctional acrylates, methacrylates or styrene with the use of a proportion of e.g. acrylic acid or methacrylic acid.

Compounds A and/or B contain at least one acrylate and/or methacrylate group. The following combinations are preferred: glycidyl acrylate and acrylic acid, glycidyl methacrylate and methacrylic acid, glycidyl methacrylate and acrylic acid, the glycidyl ether of bisphenol A or of perhydrogenated bisphenol A and acrylic acid, as well as mixtures of the combinations mentioned. The combination of glycidyl methacrylate and acrylic acid is particularly preferred. The ratio by equivalents of acid to epoxide can be varied over a wide range. However, a ratio by equivalents of 1.2:1.0 to 1.0:1.2 is preferred, more preferably 1.05:1.00 to 1.00:1.05. It may be particularly expedient to use a slight excess of one component in order to obtain especially low residual concentrations of the other component in the process product. For example, residual concentrations of acrylic acid or glycidyl methacrylate of less than 0.1 wt. % can be achieved using the process according to the invention, given a suitable choice of the equivalent ratio.

In the process according to the invention, the reaction of A with B is catalyzed by Lewis acid boron, aluminium, gallium, indium, yttrium, lanthanum, silicon, germanium, tin, arsenic, antimony, bismuth, titanium, zirconium and hafnium compounds, each of which contains at least one, preferably two or more, directly bonded di(cyclo)alkylamino groups. Bis-(dimethylamino)-dimethylsilane, tetrakis-(dimethylamino)-silane, tetrakis-(dimethylamino)-zirconium, tetrakis-(dimethylamino)-diborane, tris-(diethylamino)-aluminium dimer, tris-(dimethylamino)-aluminium dimer, and tris-(dimethylamino)-borane are preferred. Tris-(dimethylamino)-borane is particularly preferred.

The catalyst may be used in any amount, but the actual amount used is expediently restricted to the minimum required. Naturally, the optimum amount depends on the particular substances being reacted and can be determined by appropriate trials. The catalyst is preferably used in amounts of 0.05 to 5.0 wt. %, more preferably 0.1 to 1.0 wt. % and most preferably 0.1 to 0.5 wt. %, based on the weight of A and B.

The reaction is preferably performed in the presence of one or more stabilizers for acrylates and methacrylates. In addition to an oxygen-containing gas, chemical stabilizers in amounts of 0.01 to 1 wt. %, preferably 0.1 to 0.5 wt. %, based on the weight of unsaturated compounds, are suitable for avoiding premature polymerization. Such stabilizers are described, for example, in Houben-Weyl, Methoden der organischen Chemie, 4th edition, vol. XIV/1, Georg Thieme Verlag, Stuttgart 1961, p. 433 et seq. Examples include copper compounds, trivalent phosphorus compounds such as phosphites or phosphonites, sodium dithionite, sodium hydrogen sulfide, sulfur, hydrazine, phenylhydrazine, hydrazobenzene, N-phenyl-β-naphthylamine, N-phenylethanol diamine, dinitrobenzene, picric acid, p-nitrosodimethylaniline, diphenylnitrosamine, phenols (e.g. para-methoxyphenol, 2,5-di-tert.-butylhydroquinone, 2,6-di-tert.-butyl-4-methylphenol, p-tert.-butyl-pyrocatechol or 2,5-di-tert.-amyl-hydroquinone), tetramethyl-thiuram disulfide, 2-mercaptobenzthiazole, the sodium salt of dimethyl-dithiocarbamic acid, phenothiazine, and N-oxyl compounds such as 2,2,6,6-tetramethylpiperidine-N-oxide (TEMPO) or one of its derivatives.

According to the invention, 2,6-di-tert.-butyl-4-methylphenol, 2,5-di-tert.-butylhydroquinone and/or para-methoxyphenol and mixtures thereof are preferred.

The reaction can be performed in the presence of an organic solvent which is inert towards the reactants and the products. Examples are lacquer solvents such as butyl acetate, solvent naphtha, methoxypropyl acetate or hydrocarbons such as cyclohexane, methylcyclohexane or isooctane. After completion of the reaction, the solvent can be removed, e.g. by distillation, or may remain in the process product. The use of a solvent is preferably avoided.

Apart from solvents, reactive diluents may also be used. Examples of these are compounds which are recognized within the technology of radiation curing of coatings (see Römpp Lexikon Chemie, p. 491, 10th ed. 1998, Georg-Thieme-Verlag, Stuttgart). Examples include the esters of acrylic or methacrylic acid, preferably acrylic acid, and the following alcohols. Monohydric alcohols include the isomeric butanols, pentanols, hexanols, heptanols, octanols, nonanols and decanols; cycloaliphatic alcohols such as isobomol, cyclohexanol and alkylated cyclohexanols and dicyclopentanol; arylaliphatic alcohols such as phenoxyethanol and nonylphenylethanol; and tetrahydrofurfuryl alcohols. Alkoxylated derivatives of these alcohols may be also used.

Examples of dihydric alcohols include ethylene glycol, propane-1,2-diol, propane-1,3-diol, diethylene glycol, dipropylene glycol, the isomeric butanediols, neopentyl glycol, hexane-1,6-diol, 2-ethylhexanediol, tripropylene glycol and also alkoxylated derivatives of these alcohols. Preferred dihydric alcohols are hexane-1,6-diol, dipropylene glycol and tripropylene glycol. Higher functional alcohols include glycerol, trimethylolpropane, ditrimethylolpropane, pentaerythritol or dipentaerythritol or alkoxylated derivatives of these alcohols.

The reaction of A and B takes place either continuously, e.g. in a static mixer, or batchwise, e.g. in a suitable stirred vessel. When using the batchwise procedure, the components may be reacted in any sequence. Preferably, one component is initially introduced, the major portion of the catalyst and the stabilizer are added and the mix is heated with stirring. The other component is then added all at once or, preferably gradually, wherein as constant a temperature as possible is maintained by heating and using the heat of reaction. The degree of conversion is determined by analysis. This may be performed spectroscopically, e.g. by recording infrared or near infrared spectra, but it may also be performed by analysis of withdrawn samples, e.g. by titration, gas chromatography or determination of the refractive index. Both the acid content and the epoxide content, determined using titrated samples, are especially suitable as a measure of the degree of conversion of the reaction. The addition procedure and the reaction are performed at a temperature of 60 to 130° C., preferably 65 to 120° C., and more preferably 75 to 95° C.

When using the continuous procedure, temperatures above 130° C. may also be used, given a sufficiently short residence time within the minute range.

The reaction is preferably continued until an epoxide content of less than 0.2 wt. %, preferably less than 0.1 wt. % (calculated as MW 42) and an acid value below 10 mg KOH/g, preferably below 5 mg KOH/g, are achieved. If the reaction is terminated before this point, then, e.g. by the application of a vacuum or by passage of a gas which preferably contains oxygen, the residual concentration of volatile reactants may be reduced so that correspondingly low epoxide and acid contents are achieved. It is also possible to lower the epoxide content by adding small amounts of epoxide-reactive compounds such as strong acids, e.g. butyl phosphate. Residual concentrations of acid can be reduced in an analogous manner, e.g. by reaction with carbodiimides or aziridines.

The process products can be further reacted or formulated immediately or may first be stored or transported. Further reaction, e.g. with polyisocyanates, preferably takes place without further purification such as by extraction or distillation.

The process according to the invention is characterised in particular by a comparatively high selectivity. If monomeric compounds are used as A and B respectively, then the concentration of constituents in the process product which have an oligomeric or polymeric character according to gel permeation chromatography is preferably less than 35 wt. %, more preferably less than 25 wt. %.

The process products according to the invention are particularly suitable for use to prepare raw materials and formulations for materials which can be cured by actinic radiation. If they are used as intermediates for the synthesis of appropriate raw materials, then further reaction may take place, for example with the hydroxyl groups produced in the process according to the invention and/or optionally also present or by addition to double bonds which are present e.g. by the addition of compounds which contain primary and/or secondary amino groups. In particular, the hydroxyl groups can be reacted further by urethanization and/or allophanatization, using known processes.

The process products according to the invention as well as the products obtained by further chemical reactions are suitable as components of compositions which can be cured by actinic radiation such as lacquers, coatings, printing inks, sealants, impregnating resins and surface fillers.

The following examples are intended to illustrate the invention without restricting its scope. All quantities in "parts" and "%" are by weight unless otherwise indicated.

EXAMPLES

The acid value was cited in mg KOH/g of sample and was determined by titration with 0.1 mol/l NaOH solution against bromothymol blue (ethanolic solution), color change from yellow via green to blue, based on DIN 3682.

The hydroxyl value was cited in mg KOH/g of sample and was determined by titration with 0.1 mol/l methanolic KOH solution after cold acetylation with acetic anhydride, catalyzed by dimethylaminopyridine, based on DIN 53240.

The epoxide content was determined by titrating the sample dissolved in methylene chloride/acetic acid with a perchloric acid standard solution (0.1 mol/l), after the addition of tetrabutyl ammonium iodide. The amine which had been released and any basic amine present were thus determined. The basic (free) amine was determined in the same way, but without the addition of tetrabutyl ammonium iodide. The difference gave the concentration of epoxide in wt. %, calculated as CH—O—CH (MW=42 g/mol). The method of determination was based on DIN 16945.

Gel permeation chromatography (GPC): eluant THF, RI detection, integration after calibration with a polystyrene standard.

Viscosities: Rotation viscometer, measurements at 23° C.

Unless stated otherwise, percentage data is percentage by weight (wt. %).

Example 1

Preparation of an Epoxyacrylate 142.23 g of Epilox® A 19-00 (bisphenol A epoxide resin from Leuna-Harze GmbH, Leuna, Germany, with an epoxide equivalent weight of 190 g), 0.20 g of 2,6-di-tert.-butyl-4-methylphenol and 0.70 g of tris(dimethylamino)borane (Sigma-Aldrich Chemie GmbH, Taufkirchen, Germany) were initially introduced into a heatable glass flask fitted with a mechanical stirrer, thermometer and gas inlet and heated to 70° C. with stirring and the introduction of air (0.5 l/h). 56.67 g of acrylic acid were added at this temperature over the course of 45 min. Afterwards, the mixture was stirred at 90° C. and the progress of the reaction was monitored by determining the acid value of a withdrawn sample. After 4 hours the acid value was 34 mg KOH/g, after 12 h it was 8 mg KOH/g and after 15 h it was 5 mg KOH/g. The mixture was then diluted with 50.00 g of Laromer® HDDA (hexanediol diacrylate, BASF AG, Ludwigshafen, Germany) and cooled. The viscosity was 14,700 mPa.s, the color index was 48 APHA and the acid value was 5.0 mg KOH/g.

Reaction of Glycidyl Methacrylate with Acrylic Acid:

13.27 g of glycidyl methacrylate, 0.02 g of 2,6-ditert.-butyl-4-methylphenol, 6.78 g of acrylic acid and 0.10 g of one of the catalysts set forth in Table 1 were reacted each time at 80° C. in a glass vessel with a small opening and with magnetic stirring. The acid value was determined after 24 and 48 hours. If it was greater than 4 mg KOH/g after 48 hours, the batch was discarded without further analysis.

TABLE 1

| | | Test series at 80° C. | | | | |
|---|---|---|---|---|---|---|
| Ex. no. | Catalyst | Acid value after 24 h (mg KOH/g) | Acid value after 48 h (mg KOH/g) | Hydroxyl value (mg KOH/g) | GPC main signal (area %) | Note |
| C2 | Triethylamine | 12.6 | 1.8 | 220 | 68 | yellow |
| C3 | Diazabicyclooctane | 15.5 | 5.9 | 232 | 80 | yellow |
| C4 | Tin(II) octoate | gelled within 24 hours | | | | |
| C5 | Dibutyltin dilaurate | 22.0 | 11.2 | — | — | — |

TABLE 1-continued

| | | Test series at 80° C. | | | | |
|---|---|---|---|---|---|---|
| Ex. no. | Catalyst | Acid value after 24 h (mg KOH/g) | Acid value after 48 h (mg KOH/g) | Hydroxyl value (mg KOH/g) | GPC main signal (area %) | Note |
| C6 | Thiodiglycol | 14.2 | 8.3 | — | — | — |
| C7 | Triethylbenzylammonium chloride | 9.2 | 2.1 | 243 | 79 | — |
| C8 | Triphenyl phosphine | 6.6 | 1.5 | 220 | 75 | — |
| 9 | Tris(dimethylamino)-borane | 4.0 | 1.6 | 238 | 80 | — |

The catalysts in comparison examples C2 to C6 exhibit, for a given weight, much lower activity, and those in C7 and C8 a lower activity, than the catalyst in example 9 according to the invention. The reaction product was at least equal to the comparison products according to the acid value, hydroxyl value and purity (GPC analysis).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a hydroxyalkyl (meth)acrylate which comprises reacting at least one compound A which contains at least one epoxide group with at least one compound B which contains at least one carboxylic acid group, wherein A and/or B also contains at least one (meth)acrylate group, in the presence of a Lewis acid catalyst which contains at least one directly bonded di(cyclo)alkylamino group.

2. The process of claim 1 wherein 0.05 to 5.0 wt. %, based on the weight of A and B, of a Lewis acid catalyst is used.

3. The process of claim 1 wherein 0.1 to 1.0 wt. %, based on the weight of A and B, of a Lewis acid catalyst is used.

4. The process of claim 1 wherein 0.1 to 0.5 wt. %, based on the weight of A and B, of a Lewis acid catalyst is used.

5. The process of claim 1 wherein the Lewis acid catalyst comprises a boron, aluminium, zirconium and/or silicon compound which contains at least one directly bonded di(cyclo)alkylamino group.

6. The process of claim 1 wherein compound A comprises glycidyl methacrylate and/or glycidyl acrylate.

7. The process of claim 1 wherein compound B comprises acrylic acid and/or methacrylic acid.

8. The process of claim 6 wherein compound B comprises acrylic acid and/or methacrylic acid.

9. The process of claim 1 wherein compound A comprises glycidyl methacrylate and compound B comprises acrylic acid.

10. The process of claim 1 wherein the Lewis acid comprises a boron compound which contains at least one directly bonded di(cyclo)alkylamino group.

11. The process of claim 6 wherein the Lewis acid catalyst comprises a boron compound which contains at least one directly bonded di(cyclo)alkylamino group.

12. The process of claim 7 wherein the Lewis acid catalyst comprises a boron compound which contains at least one directly bonded di(cyclo)alkylamino group.

13. The process of claim 8 wherein the Lewis acid catalyst comprises a boron compound which contains at least one directly bonded di(cyclo)alkylamino group.

14. The process of claim 9 wherein the Lewis acid catalyst comprises a boron compound which contains at least one directly bonded di(cyclo)alkylamino group.

15. The process of claim 1 the Lewis acid catalyst comprises tris-(dimethylamino)-borane.

16. The process of claim 6 the Lewis acid catalyst comprises tris-(dimethylamino)-borane.

17. The process of claim 7 the Lewis acid catalyst comprises tris-(dimethylamino)-borane.

18. The process of claim 8 the Lewis acid catalyst comprises tris-(dimethylamino)-borane.

19. The process of claim 9 the Lewis acid catalyst comprises tris-(dimethylamino)-borane.

\* \* \* \* \*